United States Patent [19]

Göetz et al.

[11] 4,429,155
[45] Jan. 31, 1984

[54] PREPARATION OF AROMATIC AMINES

[75] Inventors: Norbert Göetz, Worms; Peter Jacobs, Gruenstadt; Leopold Hupfer, Friedelsheim; Herbert Toussaint, Frankenthal; Wolfgang Reiss, Ludwigshafen, all of Fed. Rep. of Germany

[73] Assignee: BASF Aktiengesellschaft, Ludwigshafen, Fed. Rep. of Germany

[21] Appl. No.: 326,419

[22] Filed: Dec. 1, 1981

[30] Foreign Application Priority Data

Dec. 4, 1980 [DE] Fed. Rep. of Germany ....... 3045719

[51] Int. Cl.$^3$ ..................... C07C 85/00; C07C 85/06; C07C 85/24
[52] U.S. Cl. ..................................... 564/402; 564/447
[58] Field of Search ............................... 564/402, 447

[56] References Cited

U.S. PATENT DOCUMENTS

| 2,714,614 | 8/1955 | Weinmayr | 564/402 X |
| 3,124,614 | 3/1964 | Dankert et al. | 564/402 |
| 3,219,702 | 11/1965 | van Verth et al. | 564/402 |
| 3,219,704 | 11/1965 | Wilder et al. | 564/402 |
| 3,347,921 | 10/1967 | Carrubba et al. | 564/402 |
| 3,361,818 | 1/1968 | Barker | 564/402 |
| 3,931,298 | 1/1976 | Wollensak | 564/402 |
| 3,960,962 | 6/1976 | Shubkin | 564/402 |
| 4,355,180 | 10/1982 | Goetz et al. | 564/402 X |

FOREIGN PATENT DOCUMENTS 1031169  3/1965  United Kingdom ................ 564/402

*Primary Examiner*—Paul F. Shaver
*Attorney, Agent, or Firm*—Keil & Witherspoon

[57] ABSTRACT

Aromatic amines (anilines) are obtained directly or via the corresponding cycloaliphatic amines by an aminating/hydrogenating reaction of phenols with ammonia and hydrogen over a supported palladium catalyst which also contains elements from group 1b, 2b or 7b of the periodic table as well as iron, cobalt or nickel, as such or in the form of their compounds, and, preferably, an inorganic base, said catalysts also having dehydrogenating properties.

6 Claims, No Drawings

PREPARATION OF AROMATIC AMINES

The present invention relates to a process for the preparation of aromatic amines from corresponding aromatic hydroxy compounds (phenols) and/or cycloaliphatic amines.

The oldest and at present still the most important method of preparing primary aromatic amines is the reduction of the corresponding nitro compounds (Houben-Weyl, Methoden der Org. Chemie, Volume 11/1, page 360 et seq.). The disadvantage of this method is that nitration of substituted aromatic compounds frequently proceeds in more than one way and isomer mixtures are almost always obtained.

Since phenols are compounds which are generally readily accessible in a pure form, it is obvious to replace the hydroxyl group with an amino group, as is the case in the synthesis of aliphatic amines, in order thus to obtain anilines with a uniform substitution pattern.

In principle, it is possible to convert phenols into cyclohexanones by partial hydrogenation (German Published Application DAS Nos. 1,124,487; 1,298,098 and 1,144,267, U.S. Pat. No. 3,124,614, Swiss Pat. No. 463,493 and German Laid-Open Application DOS No. 2,045,882) and to react the cyclohexanones with ammonia and hydrogen to give cyclohexylamines (Houben-Weyl, loc. cit., pages 611-617) and dehydrogenate the cyclohexylamines to give aromatic amines (U.S. Pat. No. 3,361,818), or to convert the cyclohexanones directly into the aromatic amines with ammonia (U.S. Pat. Nos. 3,219,702 and 3,219,704).

However, since they require several independent process steps, these routes are extremely involved and are not particularly economical.

The one-stage (direct) conversion of phenols into cyclohexylamines with ammonia and hydrogen proceeds in the presence of ruthenium or rhodium catalysts (Japanese Preliminary Published Application No. 4,034,677, French Pat. No. 1,427,543 and British Pat. No. 1,031,169). A method for directly preparing aromatic amines from phenols has also been disclosed (German Laid-Open Application DOS No. 2,208,827 and U.S. Pat. Nos. 3,931,298 and 3,960,962). In this process, the course of the reaction is said to demand the presence of a cyclohexanone compound, a certain amount of which must initially be added to the reaction mixture as a catalyst or must be produced from the phenol. It can be assumed that this process is a direct combination in sequence of the above process steps, which proceed via a cyclohexanone as an intermediate. In addition to the cyclohexanone, a hydrogenation catalyst is required in this process, and palladium appears to be preferred.

It is an object of the present invention to provide a process for the preparation of, preferably substituted, anilines from phenols or corresponding cycloaliphatic amines.

We have found that mononuclear or polynuclear aromatic amines, for example those of the general formula I

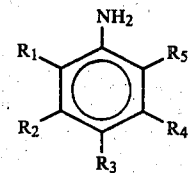

where $R_1$ to $R_5$ can each be hydrogen or identical or different substituents, or two or more together can be one substituent, are obtained in good yields, directly or via the corresponding cycloamines, when a corresponding phenol is reacted with ammonia and hydrogen at from 100° to 400° C. over a palladium catalyst which contains a basic substance and/or an element from group Ib, 2b or 7b of the periodic table, iron, cobalt or nickel. These catalysts have good dehydrogenating properties and are equally suitable for preparing the desired anilines from independently obtained cycloaliphatic amines.

Examples of the substituents are aliphatic groups of 1 to 20 carbon atoms, cycloaliphatic groups of 5 to 20 carbon atoms, aryl groups of 6 to 20 carbon atoms and aralkyl and alkylaryl groups of 7 to 20 carbon atoms. These substituents may contain oxygen and/or nitrogen as hetero-atoms, or two substituents can be linked with one another by a molecular bridge.

Depending on the reaction temperature, the catalysts according to the invention produce either predominantly cycloaliphatic or predominantly aromatic amines, the selectivity and purity being excellent; this means that formation of by-products can be almost completely suppressed. This result is surprising since, from the prior art, numerous side reactions and hence by-products, such as cyclohexanol, cyclohexanone, dicyclohexylamine, phenyl-cyclohexylamine and diphenylamine, are to be expected at elevated temperatures. By selecting the conditions, the course of the reaction can be so controlled that either saturated cyclohexylamines or the corresponding aromatic amines (anilines) are formed: formation of the aromatic amines is favored under pressures of from atmospheric to less than approx. 50 bars, whereas reaction under high pressure favors the formation of cycloaliphatic amines. 100 to 500 bars is a useful pressure range in this case.

Increasing the temperature or lowering the hydrogen pressure favors the formation of the anilines, so that in the lower range of from 150° to 230° C. the saturated (cycloaliphatic) amines are primarily obtained, and in the upper range of from 180° to 300° C. anilines are chiefly obtained. Moreover, any cyclohexylamines remaining unconverted in the upper range can be converted into anilines (Example 5b, 10) due to the dehydrogenating properties of the catalysts. The temperature may be in the range of 180° to 300° C., or as low as 180° to 200° C. when recycling unreacted cycloaliphatic amines. It should be mentioned that cyclohexylamines can easily be separated from the corresponding anilines. The essential advantage of the process and catalysts described in the present Application is due to this fact, since, if the phenols are used as starting substances, they can be completely reacted, so that troublesome and expensive separation of the phenol from the aniline, such as is necessary, for example, in the method of German Laid-Open Application DOS No. 2,208,827, is avoided.

The phenols used as starting substances are in general readily accessible compounds (Houben-Weyl, Methoden, Volume 6/1c).

According to the above formula for the desired products, a corresponding phenol can carry substituents $R_1$ to $R_5$, one or more of which can also itself be a phenol, so that the term phenol thus embraces mononuclear and polynuclear phenols. Bisphenol A is an example of a polynuclear phenol.

$R_1$ to $R_5$ can furthermore be identical or different substituents, and of course also hydrogen. Alkyl and aralkyl, each with chain lengths of 1 to 20 carbon atoms, are particularly important substituents. The substituents can also contain oxygen or nitrogen in the chain or in a heterocyclic arrangement. Adjacent substituents can form a ring with the phenol radical, so that phenols also include naphthols and partially hydrogenated naphthols.

It is true that the reaction of hydroxybenzene (phenol) itself is not of commercial interest, even though it is technically possible. Examples of other substituted phenols are o-, m- and p-cresol, o-ethylphenol, o-n-butylphenol, o-sec.-butylphenol, 2,4-dimethylphenol, 2,6-dimethylphenol, 2,3,6-trimethylphenol, 2,4,6-trimethylphenol, 2-cyclohexylphenol, 2,6-dimethyl-3-phenylphenol, 2,6-diethylphenol, 2,5-diisopropylphenol, 2,6-di-tert.-butylphenol, 2-methyl-6-sec.-butylphenol, 3-tert.-butylphenol, α-naphthol, β-naphthol and bisphenol A (=2,2-di-(p-hydroxyphenyl)-propane). The invention embraces the dehydrogenation of cycloaliphatic amines corresponding to the aforementioned phenols.

The ammonia required for conversion of the phenol into the amine can be used in the stoichiometric amount, based on the phenol employed, or in excess, even in a large excess.

Both the hydrogenating amination and the dehydrogenation process can be carried out continuously or batchwise and in the gas or liquid phase. In all cases, the catalyst can be in a fixed bed or in a fluidized bed or suspension. For the continuous procedure, a fixed-bed catalyst is preferred, and the ammonia is passed over the catalyst together with the hydrogen, as a rule in a ratio of from 10:1 to 1:10. In the batchwise procedure, hydrogen is supplied until the phenol employed has reacted completely. The aminating reaction can be carried out in the absence of solvents, or in the presence of solvents which are chemically inert under the reaction conditions. The dehydrogenating step, if carried out separately, does not need any reagent except for the cycloaliphatic amine and, naturally, the catalyst. The presence of ammonia and/or hydrogen is, however not a disadvantage, because of the activating and conserving effect on the catalyst.

Examples of solvents which can be used are methanol, ethanol, n-butanol, tetrahydrofuran, dioxane, cyclohexyl methyl ether, methylglycol, ethylglycol, 1,2-dimethoxyethane, N,N-dimethylcyclohexylamine, N-methylpiperidine, N-ethylpiperidine, N-methylmorpholine, N-methylpyrrolidine and cyclohexane. In many cases, the desired product itself is an advantageous solvent, and a part stream is recycled when appropriate dilution is desired.

The catalyst system used in the process of the invention contains on the one hand palladium, and on the other hand active additives used singly or as mixtures with one another. The active constituents of the catalyst are applied to a carrier, which can consist of aluminum oxide, silicic acid, aluminum silicate, magnesium silicate, active charcoal or spinels of aluminum, chromium or iron, and the additives which are responsible for the properties of the catalyst can be on the surface of the catalyst, or are mixed with a chemically inert material, the mixture acting as the carrier, or form a common crystal lattice with the original carrier as a result of subsequent heating (as, for example, is the case with certain metals and aluminum oxide carriers, which form spinel lattices). This means that the carrier can have an advantageous effect on the activity and life of the catalyst. Preferably, aluminum oxide is used as the carrier.

Possible additives are:

(a) Basic additives, such as oxides, hydroxides or carbonates of the alkali metals, preferably of lithium or sodium, of the alkaline earth metals, preferably of magnesium or calcium, and of the rare earth metals, preferably of cerium or praseodymium/neodymium, the latter having a similar effect; and (b) other metals, such as nickel, cobalt, manganese, zinc, cadmium and silver.

The additives can be applied at the same time as the palladium, by impregnating the carrier with solutions of, for example, nitrates, chlorides, formates or oxalates. Conversion to the oxides is effected by subsequent heating, usually at from 400° to 600° C. If spinels are to be produced with aluminum oxide carriers and suitable metals (Mg, Zn, Co, Mn, Li), the carrier must be heated to from 900° to 1,300° C. after impregnation (cf. Ullmanns Encyklopädie der technischen Chemie, 3rd Edition (1955), Volume 6, pages 242–244, and Gmelin, System No. 35, Al, Tl, 1934–1935, pages 26–28) and the palladium must then be applied in a conventional manner. Some additives, for example calcium oxide or magnesium oxide, can be mixed with a carrier such as aluminum oxide and, after the mixture has been heated at from 400° to 600° C., form a new carrier on which the palladium can be precipitated. Soluble additives, such as sodium carbonate, can be added in the form of their solutions to the product to be reacted, separately from the actual hydrogenation catalyst.

The palladium content of the catalyst is usually from 0.05 to 15% by weight, based on the carrier. The weight ratio of additives to palladium can vary, for example from 10,000:1 to 1:50, and preferably from 100:1 to 1:50. The catalyst is used, for example, in the form of extrudates having a diameter of 3 mm and a length of 10 mm, or in the form of a powder, depending on the intended application.

The compounds prepared by the process of the invention are used, for example, as intermediates for preparing active ingredients in crop protection agents (German Published Application DAS No. 2,305,495 and German Laid-Open Application DOS Nos. 2,648,008, 2,513,732 and 2,515,091).

Possible Methods of Preparing the Catalyst (a) Palladium and the additive (manganese, zinc, silver, rare earth metals and the like) in the desired amount are applied to γ-aluminum oxide in the form of extrudates or powder by impregnation of the carrier with, for example, nitrate solutions and subsequent evaporation to dryness. The carrier is then heated at 550° C. for 6 hours, and reduction is carried out in a stream of hydrogen at 300° C.

(b) The desired amount of additive (manganese, zinc, cobalt, magnesium, lithium and the like) is first applied to γ-aluminum oxide in the form of extrudates or powder by impregnation of the carrier with corresponding aqueous nitrate or formate solutions, and the carrier is dried at 150° C. The pretreated carrier is now either heated at 550° C. for 6 hours or, if spinel formation is to be achieved, heated at 1,050° C. for 6 hours. The carrier is then impregnated with aqueous palladium nitrate solution, and reduction is carried out by heating at 300° C. in a stream of hydrogen for 7 hours. If palladium-II chloride solution has been used for the impregnation, alkaline formalin solution is used for the reduction.

(c) γ-Aluminum oxide and a basic oxide (MgO or CaO) are mixed thoroughly with one another in the desired ratio. This mixture is heated to 450° C. for 6 hours and then impregnated with palladium nitrate solution, and reduction is carried out with hydrogen at 300° C. for 7 hours. After-reduction of the catalyst is carried out with 5% strength aqueous hydrazine hydrate solution, and the catalyst is then dried at 120° C.

The boiling points in the following Examples were observed at atmospheric pressure unless otherwise indicated.

EXAMPLE 1

A catalyst in the form of strands (3 mm in diameter, 10 mm in length) containing 0.5% by weight of palladium on a mixture of 19.4% by weight of magnesium oxide and 80.6% by weight of aluminum oxide is introduced into a 1.2 l pressure-resistant cylindrical tube, as the reactor, and is heated at 220° C. 100 g of 2,6-dimethylphenol per hour are passed over the catalyst under atmospheric pressure. At the same time, a gaseous mixture of 250 liters (S.T.P.) of ammonia and 250 liters (S.T.P.) of hydrogen per hour is passed through in co-current. As soon as it leaves the reactor, the reaction product is cooled. According to analysis by gas chromatography, it consists of 78% by weight of 2,6-dimethylaniline (boiling point=216° C.) and 22% by weight of 2,6-dimethylcyclohexylamine (boiling point=167°–168° C.). The two amines can easily be separated by distillation; the cyclohexylamine can be either recycled into the reaction zone or dehydrogenated to 2,6-dimethylaniline separately (see Example 5b, 10). When the 2,6-dimethylphenol employed has been converted completely into 2,6-dimethylaniline, 93.5 g of 2,6-dimethylaniline are obtained per 100 g of 2,6-dimethylphenol, corresponding to 94% of the calculated yield.

EXAMPLE 2

The procedure described in Example 1 is followed, using a catalyst which contains 0.5% by weight of palladium on a mixture of 19.4% by weight of calcium oxide and 80.6% by weight of aluminum oxide. Starting from m-tert.-butylphenol, m-tert.-butylaniline is obtained (boiling point=72°–73° C./0.27 mbar) in a yield of 96%.

EXAMPLE 3

The procedure described in Example 1 is followed, using a catalyst which contains 1.0% by weight of palladium on a cobalt/aluminum spinel. Aniline (boiling point=184° C.) is obtained from phenol in a yield of 96%.

EXAMPLE 4

The procedure described in Example 1 is followed, using a catalyst which contains 1.0% by weight of palladium on a lithium/aluminum spinel. Starting from 2-ethylphenol, 2-ethylaniline (boiling point=210° C.) is obtained in a yield of 93%.

EXAMPLE 5

(a) A catalyst which consists of 10% by weight of palladium, 5% by weight of praseodymium oxide and aluminum oxide, as the remainder, in the form of extrudates (4 mm in diameter, 10 mm in length) is introduced into a 1 l cylindrical reaction tube. A mixture of 30 g of 2,3,6-trimethylphenol, 100 g of 2,3,6-trimethylcyclohexylamine and 1,000 g of liquid ammonia per hour is passed over this catalyst at 180° C. At the same time, 200 liters (S.T.P.) of hydrogen are passed in co-current through the reaction tube under a pressure of 250 bar. The product issuing from the tube is cooled under superatmospheric pressure and then let down. About 130 g per hour of crude product, which consists of 2,3,6-trimethylcyclohexylamine and can be further reacted without purification, are thereby obtained; for a continuous procedure, an appropriate amount of the amine is in each case recycled and mixed with fresh phenol.

(b) 100 g per hour of trimethylcyclohexylamine from the preceding process step are passed, at 210° C. and under atmospheric pressure, over a catalyst consisting of 1.0% by weight of palladium and 0.5% by weight of praseodymium oxide on aluminum oxide in a 1 l cylindrical reaction tube. At the same time, a gaseous mixture of 200 liters (S.T.P.) of ammonia and 10 liters (S.T.P.) of hydrogen is passed through the reaction tube in co-current with the liquid. The resulting reaction product is cooled and distilled. 94.5 g of 2,3,6-trimethylaniline (boiling point=119° C./27 mbar) are obtained per 100 g of 2,3,6-trimethylphenol, corresponding to a yield of 95%.

EXAMPLE 6

(a) A mixture of 54.5 g of 2,3,6-trimethylphenol, 41 g of liquid ammonia and 6 g of the catalyst used in Example 5(a) is hydrogenated at 230° C. under a constant hydrogen pressure of 250 bar for 30 hours in a 300 ml stirred autoclave. According to analysis by gas chromatography, the reaction product consists of 96% by weight of 2,3,6-trimethylcyclohexylamine and 4% by weight of 2,3,6-trimethylcyclohexanol.

(b) The above procedure is followed, at 250° C. The reaction product consists of 51% by weight of 2,3,6-trimethylcyclohexylamine, 3% by weight of 2,3,6-trimethylcyclohexanol and 46% by weight of 2,3,6-trimethylaniline.

(c) The reaction is carried out at 275° C. The reaction product consists of 29% by weight of 2,3,6-trimethylcyclohexylamine, 3% by weight of 2,3,6-trimethylcyclohexanol and 68% by weight of 2,3,6-trimethylaniline.

EXAMPLE 7

The procedure described in Example 6c is followed, using a catalyst which contains 5.0% by weight of palladium, 1.0% by weight of manganese and 5.0% by weight of silver, the remainder being aluminum oxide. Using this catalyst, α-naphthol is converted into α-naphthylamine (melting point 49° C.) with a selectivity of 92%.

EXAMPLE 8

The procedure described in Example 6c is followed, using a catalyst which contains 10% by weight of palladium, 0.11% by weight of zinc and 0.10% by weight of cadmium, the remainder being aluminum oxide. Using this catalyst, 2,6-dimethyl-3-phenyl-phenol is converted to 2,6-dimethyl-3-phenylaniline (boiling point=121° C./0.22 mbar) with a selectivity of 91%.

EXAMPLE 9

The procedure described in Example 6b is followed, using a catalyst which contains 5.0% by weight of palladium and 2.5% by weight of cerium-IV oxide, the remainder being aluminum oxide. Using this catalyst, 2,6-dimethyl-3-(p-methoxyphenyl)-phenol is converted to 2,6-dimethyl-3-(p-methoxyphenyl)-aniline (boiling point=151° C./0.5 mbar) with a selectivity of 85%.

EXAMPLE 10

A mixture of 56.5 g of 2,3,6-trimethylcyclohexylamine, dissolved in 120 g of toluene, and 6 g of the catalyst from Example 5 is heated in a 300 ml stirred autoclave at 250° C. under autogenous pressure (about 40 bar), for 10 hours. The reaction product (without taking into account the solvent) consists of 52% by weight of 2,3,6-trimethylcyclohexylamine and 48% by weight of 2,3,6-trimethylaniline.

EXAMPLE 11

A mixture of 54 g of 2,3,6-trimethylaniline, 41 g of liquid ammonia and 6 g of catalyst composed of 10% by weight of palladium and 5% by weight of praseodymium oxide on aluminum oxide is hydrogenated at 230° C. and under a hydrogen pressure of 250 bar in a 300 ml stirred autoclave until the pressure remains constant. The reaction product consists of pure 2,3,6-trimethylcyclohexylamine (boiling point=78°-81° C./23 mm Hg).

EXAMPLE 12

1.650 kg of 2,6-dimethylphenol and 150 g of a pulverulent catalyst which contains 5.0% by weight of palladium and 2.5% by weight of praseodymium oxide, the remainder being aluminum oxide, are introduced into a 10 l stirred autoclave. The autoclave is closed and 1.370 kg of ammonia are forced in. The mixture is then heated to 230° C. and a pressure of 200 bar is established by forcing in hydrogen. The mixture is kept at the reaction temperature until a constant pressure is achieved (about 8 hours). It is then left to cool, and is filtered to give 1.710 kg of crude 2,6-dimethylcyclohexylamine (a mixture of 3 stereoisomeric 2,6-dimethylcyclohexylamines). The crude product is distilled to give 1.685 kg of 2,6-dimethylcyclohexylamine, boiling point=167°-168° C., corresponding to a yield of 98%.

COMPARATIVE EXAMPLE TO EXAMPLE 12

If a catalyst consisting of 5.0% by weight of palladium on aluminum oxide is used instead of the above catalyst, under otherwise identical conditions, a reaction product which, according to its amine number and analysis by gas chromatography, contains 87% by weight of 2,6-dimethylcyclohexylamine is obtained, the remainder being 2,6-dimethylcyclohexanol isomers.

EXAMPLE 13

The procedure described in Example 12 is followed, at 200° C. and using a catalyst which contains 0.5% by weight of palladium on a mixture of 80.6% by weight of aluminum oxide and 19.4% by weight of calcium oxide. With this catalyst also, 2,6-dimethylcyclohexylamine is obtained, with complete conversion, in a yield of 98%.

EXAMPLE 14

The procedure described in Example 12 is followed, at 180° C. and using a catalyst which contains 1.0% by weight of palladium on a cobalt/aluminum spinel, as the carrier. 2,6-Dimethylcyclohexylamine is obtained in a yield of 94% of theory.

EXAMPLE 15

A mixture of 550 g of 2,3,6-trimethylphenol and 510 g of ammonia and 50 g of catalyst which contains 5.0% by weight of palladium, 1.0% by weight of manganese and 5.0% by weight of silver on aluminum oxide in powder form is hydrogenated at 220° C. and under a hydrogen pressure of 200 bar in a 3 l rolling autoclave. The mixture is cooled and filtered and the filtrate is distilled. 546 g of 2,3,6-trimethylcyclohexylamine, boiling point=78°-81° C./22 mbar, are obtained, corresponding to a yield of 96%.

EXAMPLE 16

The procedure described in Example 15 is followed, starting from o-cresol and using a catalyst which contains 10% by weight of palladium, 0.11% by weight of zinc and 0.1% by weight of cadmium on aluminum oxide. 2-Methylcyclohexylamine, boiling point=147° C., is obtained in a yield of 98%.

EXAMPLE 17

Phenol is reacted over a catalyst consisting of 5.0% by weight of palladium and 2.5% by weight of Ce-IV oxide on aluminum oxide, by the procedure described in Example 15. Cyclohexylamine, boiling point=134° C., is obtained in a yield of 95%.

EXAMPLE 18

A mixture of 46 g of bisphenol A (2,2-bis-(4-hydroxyphenyl)-propane), 41 g of ammonia and 6 g of catalyst (10% by weight of palladium and 5% by weight of praseodymium oxide on aluminum oxide) is hydrogenated at 200° C. and under a hydrogen pressure of 250 bar in a 300 ml stirred autoclave. The product is taken up in methanol, the mixture is filtered, the solvent is distilled from the filtrate under normal pressure and the residue is distilled under reduced pressure. 45 g of dihexylane (2,2-bis-(4-aminocyclohexyl)-propane, boiling point=144°-147° C./0.4 mbar) are thereby obtained, corresponding to a yield of 94%.

EXAMPLE 19

The procedure described in Example 18 is followed, but 2,6-dimethyl-3-phenyl-phenol is reacted by also adding 5 g of saturated aqueous sodium carbonate solution to the reaction mixture and using a catalyst consisting of 0.5% by weight of palladium on aluminum oxide. 2,6-Dimethyl-3-cyclohexyl-cyclohexylamine (boiling point=95°-98° C./0.22 mbar) is obtained in a yield of 95%.

EXAMPLE 20

The procedure described in Example 18 is followed, using 2,2-dimethyl-5-hydroxychromane as the starting material and a catalyst composed of 5.0% by weight of palladium and 1.0% by weight of manganese on aluminum oxide. 2,2-Dimethyl-5-amino-hexahydrochromane (boiling point=128°-131° C./27 mbar) is obtained in a yield of 97%.

EXAMPLE 21

The procedure described in Example 18 is followed, using 2-ethylphenol as the starting material and a catalyst composed of 1.0% by weight of palladium on a lithium/aluminum spinel. 2-Ethylcyclohexylamine (boiling point=68°-70° C./27 mbar) is obtained in a yield of 95%.

EXAMPLE 22

The procedure described in Example 18 is followed, using 3-tert.-butylphenol as the starting material and a catalyst composed of 1.0% by weight of palladium and 0.5% by weight of praseodymium oxide on aluminum oxide. 3-Tert.-butylcyclohexylamine (boiling point=84°-85° C./27 mbar) is obtained in a yield of 97%.

EXAMPLE 23

(a) A catalyst in the form of extrudates (3 mm in diameter, 10 mm in length) consisting of 0.5% by weight of palladium on a mixture of 19.4% by weight of magnesium oxide and 80.6% by weight of aluminum oxide is introduced into a 1.2 l cylindrical tube and heated to 160° C. 100 g of 2,6-dimethylphenol per hour are passed over this catalyst bed under normal pressure. At the same time, a gaseous mixture of 200 liters (S.T.P.) of ammonia and 300 liters (S.T.P.) of hydrogen per hour is passed through the reaction tube in co-current. The reaction product is cooled. According to analysis by gas chromatography, it consists of 94% by weight of 2,6-dimethylcyclohexylamine and 6% by weight of 2,6-dimethylaniline.

(b) 100 g of the reaction product from stage (a) and 6 g of catalyst (composition as described under 23a, but in powder form) are hydrogenated at 230° C. and under a hydrogen pressure of 200 bar in a 300 ml stirred autoclave until the pressure remains constant. According to analysis of the reaction product by gas chromatography, the 2,6-dimethylaniline has thereby been completely converted to 2,6-dimethylcyclohexylamine.

EXAMPLE 24

The procedure described in Example 23a is followed (without after-hydrogenation), using 2,6-dimethyl-3-phenylphenol as the starting material. 2,6-Dimethyl-3-phenylcyclohexylamine (boiling point=103°-105° C./0.13 mbar) is obtained as the end product in a yield of 92%.

EXAMPLE 25

A catalyst consisting of 1.0% by weight of palladium and 0.5% by weight of praseodymium oxide, the remainder being aluminum oxide, in extrudate form is introduced into a 1 l cylindrical reaction tube and is heated to 200° C. A mixture of 60 g of 2,6-dimethylphenol and 360 g of liquid ammonia per hour is passed over this catalyst bed. At the same time, 100 liters (S.T.P.) of hydrogen are passed in co-current through the reaction tube under a pressure of 200 bar. The reaction product which leaves the tube is cooled under superatmospheric pressure and is then let down. About 62 g of crude product, which gives 60 g of pure 2,6-dimethylcyclohexylamine (corresponding to a yield of 96%) on distillation, are thereby obtained per hour.

EXAMPLE 26

Preparation of 2,6-dimethylcyclohexylamine

A catalyst in the form of extrudate (3 mm in diameter, 10 mm in length) containing 0.5% by weight of palladium on a mixture of 19.4% by weight of magnesium oxide and 80.6% by weight of aluminum oxide is introduced into a 1.2 l cylindrical tube, as the reactor, and is heated to 130° C. 100 g of 2,6-dimethylphenol per hour are passed over the catalyst under atmospheric pressure. At the same time, a gaseous mixture of 250 liters (S.T.P.) of ammonia and 250 liters (S.T.P.) of hydrogen per hour are passed through in co-current. As soon as it leaves the reactor, the reaction product is cooled. According to analysis by gas chromatography, it consists of 96.4% by weight of 2,6-dimethylcyclohexylamine (boiling point=167°-168° C.) and 3.6% by weight of 2,6-dimethylaniline (boiling point=216° C.). The two amines can easily be separated from one another by distillation. In this manner, 100 g of 2,6-dimethylphenol give 97.5 g of 2,6-dimethylcyclohexylamine, corresponding to 93.5% of the calculated yield.

EXAMPLE 27

A catalyst containing 0.5% by weight of palladium on a magnesium/aluminum spinel is introduced into a 1.2 l reaction tube and heated to 210° C. 100 g of 2,6-dimethylcyclohexylamine (mixture of 3 stereoisomeric compounds) per hour are passed over this catalyst at atmospheric pressure. At the same time, a gas mixture of 100 liters (S.T.P.) of hydrogen and 100 liters (S.T.P.) of ammonia per hour is passed in co-current through the reaction tube. The reaction product is cooled as soon as it leaves the reactor. According to analysis by gas chromatography, it consists of 1.8% by weight of 2,6-dimethylcyclohexylamine and 98.2% by weight of 2,6-dimethylaniline. The reaction product is worked up by distillation; per 100 g of starting material there is obtained 92.5 g of 2,6-dimethylaniline having a boiling point of 216° C., corresponding to a yield of 97% of the theory. After 1200 hours' operation the catalyst still showed no loss in activity.

EXAMPLE 28

The procedure described in Example 27 is followed, using a catalyst which contains 1.0% by weight of palladium on a lithium/aluminum spinel. Starting from 3-tert-butylcyclohexylamine, there is obtained m-tert-butylaniline (boiling point=72°-73° C./0.27 mbar) in a yield of 95% of the theory.

EXAMPLE 29

The procedure described in Example 27 is followed, using a catalyst which contains 1.0% by weight of palladium on a zinc/aluminum spinel and starting from 2,6-diisopropylcyclohexylamine. 2,6-Diisopropylaniline (boiling point=257° C.) is obtained in a yield of 93% of the theory.

EXAMPLE 30

The procedure described in Example 27 is followed, using a reaction temperature of 250° C. and a catalyst which contains 0.5% by weight of palladium on a mixture of 19.4% by weight of calcium oxide and 80.6% by weight of aluminum oxide, and starting from 2-ethylcyclohexylamine. o-Ethylaniline (boiling point=210° C.) is obtained in a yield of 95% of the theory.

EXAMPLE 31

The procedure described in Example 27 is followed, using a catalyst which contains 1.0% by weight of palladium on a cobalt/aluminum spinel and starting from 2,6-diethylcyclohexylamine. 2,6-Diethylaniline (boiling point=243° C.) is obtained in a yield of 96% of theory.

EXAMPLE 32

A mixture of 60 g of 1,2,3,4-tetrahydro-1-naphthylamine, dissolved in 150 g of toluene, and 6 g of a catalyst which contains 5.0% by weight of palladium and 2.5% by weight of cerium-IV oxide on aluminum oxide is heated in a 300 ml stirred autoclave at 260° C. under autogenous pressure (60 bar), for 10 hours. The reaction product (without taking into account the solvent) consists of 63% by weight of α-naphthylamine (melting point=49° C.) and 37% by weight of starting material.

EXAMPLE 33

The procedure described in Example 32 is followed, using a catalyst which contains 5% by weight of palladium, 1% by weight of manganese and 5% by weight of silver on aluminum oxide and starting from 2,6-dimethyl-3-phenyl-cyclohexylamine. The reaction product obtained is a mixture of 56% by weight of 2,6-dimethyl-3-phenyl-aniline (boiling point=121° C./0.2 mbar) and 44% by weight of starting product.

EXAMPLE 34

The procedure described in Example 32 is followed, using a catalyst which contains 10% by weight of palladium, 0.11% by weight of zinc and 0.1% by weight of cadmium on aluminum oxide and starting from 2,6-dimethyl-3-(p-methoxyphenyl)-cyclohexylamine. The reaction product obtained is a mixture of 48% by weight of 2,6-dimethyl-3-p-methoxyphenyl-aniline (boiling point=151° C./0.4 mbar) and 52% by weight of starting material.

EXAMPLE 35

The procedure described in Example 32 is followed, using a catalyst which contains 10% by weight of palladium and 5% by weight of praseodymium oxide on aluminum oxide and starting from 3-(4'-methyl-tetrahydropyran-2-yl)-cyclohexylamine. The reaction product is a mixture of 61% by weight of m-(4-methyltetrahydropyran-2-yl)-aniline (boiling point=112° C./0.13 mbar) and 39% by weight of starting material.

EXAMPLE 36

1 l of catalyst is introduced into a fluidized-bed reactor having a capacity of 1.2 l. The catalyst contains 0.5% by weight of palladium and 0.1% by weight of zinc on $Al_2O_3$ and has a particle size of 0.2 to 0.6 mm. The temperature of the reactor is adjusted to 220° C. and an appropriately preheated mixture of 200 l (S.T.P.) of ammonia and 200 l (S.T.P.) of hydrogen per hour is fed in. 100 g of cyclohexylamine per hour is passed through the resulting fluidized bed of catalyst. The reaction product is obtained by cooling the off-gas; it is then subjected to distillation. Per 100 g of cyclohexylamine used there is obtained 89.5 g of aniline (boiling point=184° C.), corresponding to a yield of 95% of the theory.

We claim:

1. A process for the preparation of cycloaliphatic or aromatic amines (I, Ia)

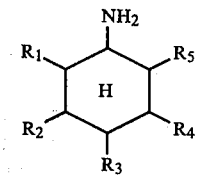

or

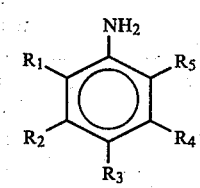

wherein each $R_1$ to $R_5$ may be hydrogen or a substituent selected from the group consisting of alkyl, cycloalkyl, aryl, arylalkyl and alkylaryl, said substituent either containing or being free of oxygen and/or nitrogen atoms, wherein each $R_1$ to $R_5$ may be linked to its neighboring R by a molecular bridge which comprises: reacting either a corresponding aromatic hydroxy compound (phenol) with ammonia and hydrogen or a corresponding cycloaliphatic amine which is obtained as an intermediate or obtained independently, with or without ammonia and/or hydrogen at an elevated temperature in the presence of a supported palladium catalyst which contains a basic substance and/or an element from group 1b, 2b or 7b of the periodic table, iron, cobalt or nickel.

2. The process of claim 1, wherein the catalyst contains, as the basic substance, an oxide, hydroxide or carbonate of an alkali metal or of an alkaline earth metal.

3. The process of claim 1, wherein the catalyst contains, as the basic substance, an oxide, hydroxide or carbonate of a rare earth metal.

4. The process of claim 2, wherein the catalyst contains a magnesium compound.

5. The process of claim 3, wherein the catalyst contains a praseodymium/neodymium compound or a cerium compound.

6. The process of claim 1, wherein a compound of the formula Ia is obtained by reacting a corresponding aromatic phenol with ammonia and hydrogen at a temperature of from about 180° to 300° C. over the supported palladium catalyst.

* * * * *